United States Patent [19]

Don et al.

[11] 4,392,001

[45] Jul. 5, 1983

[54] PROCESS FOR THE PREPARATION OF A CYCLOALKENE THROUGH PARTIAL HYDROGENATION OF THE CORRESPONDING AROMATIC HYDROCARBON

[75] Inventors: Johannes A. Don, Veenendaal; Joseph J. F. Scholten, Sittard, both of Netherlands

[73] Assignee: Stamicarbon, B.V., Geleen, Netherlands

[21] Appl. No.: 335,817

[22] Filed: Dec. 30, 1981

[30] Foreign Application Priority Data

Dec. 31, 1980 [NL] Netherlands .......................... 8007111
Sep. 2, 1981 [NL] Netherlands .......................... 8104067

[51] Int. Cl.³ .............................................. C07C 5/10

[52] U.S. Cl. ...................................... 585/269; 585/273
[58] Field of Search ................................. 585/269, 273

[56] References Cited

U.S. PATENT DOCUMENTS

3,912,787 10/1975 Nowack et al. ..................... 585/269
4,197,415  4/1980 Hideyuki et al. ................... 585/269

*Primary Examiner*—Curtis R. Davis

[57] ABSTRACT

The invention relates to a process for the preparation of a cycloalkene through partial hydrogenation of the corresponding aromatic hydrocarbon in the gas phase in the presence of a ruthenium catalyst. This hydrogenation process is carried out in the presence of water vapor.

11 Claims, No Drawings

PROCESS FOR THE PREPARATION OF A CYCLOALKENE THROUGH PARTIAL HYDROGENATION OF THE CORRESPONDING AROMATIC HYDROCARBON

BACKGROUND OF THE INVENTION

The invention relates to a process for preparing cycloalkenes, in particular cyclohexene, by partially hydrogenating the corresponding aromatic hydrocarbon, in particular benzene, in the gas phase in the presence of water vapor and in the presence of a ruthenium catalyst.

An already known process is described in GB Pat. No. 1,094,911, now laid open to public inspection, the disclosure of which is incorporated herein by reference. According to this known process, the aromatic hydrocarbon (in the vapor phase) being converted is brought into contact with metallic ruthenium, for instance ruthenium-black, together with hydrogen and from 5 to 50% by weight (relative to the hydrocarbon) of an alcohol, at a temperature of 15° C. to 150° C. The ruthenium may be employed on a support.

From an experiment, it appears that it is only possible to prepare cyclohexene from benzene in the gasphase according to this already known process at a conversion of only 10% and a selectivity of only 7%.

This reveals the great disadvantage of this known process: the very low selectivity to the desired alkene while also at a low rate of conversion of the hydrocarbon.

From GB Pat. No. 1,381,048 which has been laid open to public inspection, the disclosure of which is incorporated herein by reference, it is known to hydrogenate benzene to cyclohexene in the presence of water. However, this process is a liquid-phase process in which the water is used together with an alkaline substance to maintain a liquid phase at pH above 7.5.

However, liquid-phase hydrogenation has major drawbacks. Among other things, liquid-phase hydrogenation is not a very safe process, is a much more difficult process to operate continuously, and demands a relatively higher total pressure than gas-phase hydrogenation. Liquid-phase hydrogenation processes also require more complex equipment particularly for separating the reactants from the catalyst suspension.

DESCRIPTION OF THE PRESENT INVENTION

The gas-phase process according to the present invention yields a relatively much higher selectivity, to the desired cycloalkene, than the already known gas-phase processes. According to the present invention the preparation of a cycloalkene through partial hydrogenation of the corresponding aromatic hydrocarbon in the gas phase in the presence of a ruthenium catalyst is characterized in that this partial hydrogenation is carried out in the presence of water vapor.

Advantageously water vapor, at a partial pressure between about 50% to about 99%, and in particular between about 75% and about 95%, of its saturation pressure under the prevailing process conditions is used. Advantageously, the hydrocarbon being converted to a cycloalkene is present at a partial pressure ranging from about 1% to about 99%, of its saturation pressure under the prevailing process conditions. In particular, this partial hydrocarbon pressure ranges from about 10% to about 95% and more particularly from about 25% to about 95%. The water may also be formed in situ from oxygen and hydrogen.

The process according to the invention may be conducted batchwise or continuously.

The process according to the present invention should be carried out at a temperature between about 250° K. and about 600° K., in particular between about 290° K. and about 500° K., at a pressure between about 0.01 MPa and about 10 MPa. Although higher and lower pressures are practical they do not offer any advantage.

The ruthenium catalyst used in the process according to the invention is by preference metallic Ru. This ruthenium catalyst may be carried on a catalyst support. Preferably a hydrophobic catalyst support is employed such as, for example, porous corundum, silica dehydrated at high temperature, silanized silica or mixtures of such hydrophobic support materials.

Besides Ru, the ruthenium catalyst may also contain one or more different metals or compounds of metals (e.g., oxides). Preferably base metals such as Fe, Cr, Ni, Ge, Pb, Zn and more particularly Na are contained in the Ru catalyst employed. Advantageously, the catalyst contains about 0.1% to about 10% by weight Na, relative to the ruthenenium in the catalyst. Measurements show that the presence of Na, e.g., approximately 1% by weight of $Na_2O$, causes a dramatic and sharp improvement in the catalyst stability.

Before being used in the partial hydrogenation, the ruthenium catalyst preferably undergoes preliminary treatment with water, for instance by passing hydrogen saturated with water vapor over this catalyst for about 0.1 to about 1 hours.

By preference, the surface of the catalyst is covered with as little halogen, notably chlorine, as possible since the activity of the catalyst is greatly reduced by halogen deposits. The commonest way of preparing metallic ruthenium is by reducing technically pure $RuO_2$ at about 575° K. to about 675° K. The chlorine deposits present on or in (approximately 0.4% by weight) the technically pure $RuO_2$ are hardly removed during this process. Therefore, the technically pure $RuO_2$ is advantageously rendered substantially chlorine-free before reduction, by treating it with air at a high temperature of, for instance, about 1250° K. to about 1500° K. for a period of time which may be, for example, from about 0.1 hours to about 10 hours long. Alternatively, practically chlorine-free $RuO_2$ which has been prepared by converting $RuCl_3$ with air at a temperature above 1000° K. and preferably below 1400° K. can be employed in the present invention.

In the process according to the invention, the reaction product consists of a mixture of cycloalkene, cycloalkane, water and unconverted starting materials. This mixture is extremely well suited for the conversion of the cycloalkene, with the water present in the reaction product, into cycloalkanol. Extra water may be added if necessary. This hydration process may be effected in any known way.

The invention will be elucidated with reference to the following non-limiting examples.

The Ru catalyst employed in the examples consisted of Ru powder obtained by first heating technically pure $RuO_2$ in air for about 1 hour at about 1250° K. to about 1500° K. and then subsequently reducing this $RuO_2$ with hydrogen.

In examples 1 and 2 the thus prepared Ru powder also underwent preliminary treatment with water by passing hydrogen gas saturated with water vapor over the Ru powder for 10 minutes (high selectivities resulted).

EXAMPLE 1

At 295° K. and 110 kPa per minute, 30 cm$^3$ (NTP) of a gas mixture consisting of 0.8 molar parts of water, 1 molar part of benzene and 30 molar parts of hydrogen was passed over 6.5 mg Ru powder. At a conversion of 6%, 0.16 mole of cyclohexene was formed per mole of converted benzene, i.e., a selectivity of 16%.

EXAMPLE 2

At 318° K. and 110 kPa per minute, 21 cm$^3$ (NTP) a gas mixture consisting of 1.3 molar parts of water, 1 molar part of benzene, 4 molar parts of hydrogen and 12 molar parts of helium was passed over 7.2 mg Ru powder. At a conversion of 49%, 0.21 mole of cyclohexene was formed per mole of converted benzene; at a conversion of 20%, 0.42 mole of cyclohexene was formed per mole of converted benzene, and at a conversion of 3.4%, 0.65 mole of cyclohexene was formed per mole of converted benzene, i.e., a selectivity of 65%.

EXAMPLE 3

At 295° K. and 110 kPa per minute, 30 ml (NTP) a gas mixture consisting of 0.8 molar parts of water, 1 molar part of benzene and 30 molar parts of hydrogen was passed over 3 mg Ru powder. At a conversion of 22%, 0.08 mole of cyclohexene was formed per mole of converted benzene.

While the invention has been illustrated by the conversion of benzene to cyclohexene, it will be appreciated that other monocyclic aryl hydrocarbon starting materials may equally well be employed to form the corresponding monocyclic cycloalkene products.

What is claimed is:

1. In processes for preparing a cycloalkene by partially hydrogenating the corresponding aromatic hydrocarbon in the presence of a catalyst, the improvement consisting essentially in the combination of partially hydrogenating an aromatic hydrocarbon in the gas-phase in the presence of water vapor and in the presence of a ruthenium catalyst.

2. Process according to claim 1, wherein said cycloalkene is cyclohexene and said aromatic hydrocarbon is benzene.

3. Process according to claim 1, wherein said partial hydrogenation is carried out at a temperature between about 250° K. and about 600° K.

4. Process according to claim 1 or 3, wherein said partial hydrogenation is carried out at a temperature between about 290° K. and about 500° K.

5. Process according to claim 1, 2, or 3, wherein said partial hydrogenation is carried out at a pressure between about 0.01 MPa and about 10 MPa.

6. Process according to claims 1, 2, or 3, wherein said partial hydrogenation is carried out in the presence of water vapor at a water vapor partial pressure between 50% and 99% of the saturation pressure of said water vapor under the prevailing process conditions.

7. Process according to claim 1, wherein said partial hydrogenation is carried out at a partial pressure of said water vapor between about 75% and about 951% of the saturation pressure of said water vapor under the prevailing process conditions.

8. Process according to claim 7, wherein said partial hydrogenation is carried out at a hydrocarbon partial pressure of between about 1% and about 99% of the saturation pressure of said hydrocarbon under the prevailing process conditions.

9. Process according to claim 8, wherein said hydrocarbon partial pressure is between about 10% and about 95% of the saturation pressure of said hydrocarbon under the prevailing process conditions.

10. Process according to claim 9, wherein said hydrocarbon partial pressure is between about 25% and about 95% of the saturation pressure of said hydrocarbon under the prevailing process conditions.

11. Process according to claim 1 wherein said ruthenium catalyst is carried on a hydrophobic catalyst support.

* * * * *